United States Patent
MacQueen et al.

(10) Patent No.: US 6,399,713 B1
(45) Date of Patent: Jun. 4, 2002

(54) HYDROCARBON-TERMINATED POLYETHER-POLYAMIDE BLOCK COPOLYMERS AND USES THEREOF

(75) Inventors: Richard C. MacQueen, Phillipsburg, NJ (US); Mark S. Pavlin, Savannah, GA (US)

(73) Assignee: Arizona Chemical Company, Jacksonville, FL (US)

( * ) Notice: Subject to any disclaimer, the term of this patent is extended or adjusted under 35 U.S.C. 154(b) by 0 days.

(21) Appl. No.: 09/769,081

(22) Filed: Jan. 24, 2001

(51) Int. Cl.$^7$ ............................................. C08L 77/00
(52) U.S. Cl. ........................ 525/408; 525/425; 525/432
(58) Field of Search ................................ 525/408, 425, 525/432

(56) References Cited

U.S. PATENT DOCUMENTS

| | | | |
|---|---|---|---|
| 3,156,572 A | 11/1964 | Carlick et al. ................. 106/27 |
| 3,962,122 A | 6/1976 | Trial .......................... 252/392 |
| 4,066,585 A | 1/1978 | Schepp et al. ................. 260/18 |
| 4,165,303 A | 8/1979 | Schlossman et al. .......... 260/22 |
| 4,233,170 A | 11/1980 | Genjida et al. ................ 252/73 |
| 4,452,922 A | 6/1984 | Speranza et al. ............. 521/137 |
| 4,735,746 A | 4/1988 | Speranza et al. ............. 252/524 |
| 4,751,272 A | 6/1988 | Okita et al. .................. 525/398 |
| 4,795,581 A | 1/1989 | Nieh et al. .................... 252/77 |
| 4,830,671 A | 5/1989 | Frihart et al. ................ 106/27 |
| 4,839,424 A | 6/1989 | Murabayashi ................ 525/92 |
| 4,871,804 A | 10/1989 | Murabayashi ................ 525/92 |
| 4,889,560 A | 12/1989 | Jaeger et al. ................. 106/27 |
| 4,914,162 A | 4/1990 | Leoni et al. ................. 525/420.5 |
| 4,946,933 A | 8/1990 | Speranza et al. ......... 528/339.3 |
| 5,053,484 A | 10/1991 | Speranza et al. ............ 528/338 |
| 5,086,162 A | 2/1992 | Speranza et al. ............ 528/339 |
| 5,091,572 A | 2/1992 | Speranza et al. ............ 564/139 |
| 5,093,382 A | 3/1992 | Speranza et al. ............ 521/157 |
| 5,118,785 A | 6/1992 | Speranza et al. ............ 528/347 |
| 5,120,600 A | 6/1992 | Suppiah ....................... 428/323 |
| 5,124,412 A | 6/1992 | Catena et al. ............. 525/420.5 |
| 5,128,441 A | 7/1992 | Speranza et al. ............ 528/335 |
| 5,130,382 A | 7/1992 | Speranza et al. ............ 525/420 |
| 5,138,097 A | 8/1992 | Speranza et al. ............ 564/153 |
| 5,139,677 A | 8/1992 | Pasternak ................... 210/640 |
| 5,140,097 A | 8/1992 | Speranza et al. ............ 528/342 |
| 5,143,854 A | 9/1992 | Pirrung et al. ............... 436/518 |
| 5,178,646 A | 1/1993 | Barber, Jr., et al. ........... 51/298 |
| 5,191,006 A | 3/1993 | Matsumoto et al. ......... 524/310 |
| 5,194,638 A | 3/1993 | Frihart et al. ................ 554/47 |
| 5,270,353 A | 12/1993 | Nakano et al. .............. 523/214 |
| 5,286,288 A | 2/1994 | Tobias et al. ............. 106/20 B |
| 5,324,812 A | 6/1994 | Speranza et al. ............ 528/338 |
| 5,342,918 A | 8/1994 | Howelton et al. ........... 528/318 |
| 5,350,789 A | 9/1994 | Sagawa et al. .............. 524/313 |
| 5,455,309 A | 10/1995 | Albini et al. ............. 525/420.5 |
| 5,455,326 A | 10/1995 | Parker ......................... 528/335 |
| 5,500,209 A | 3/1996 | Ross et al. .................... 426/66 |
| 5,585,057 A | 12/1996 | Trotta ......................... 264/130 |
| 5,589,396 A | 12/1996 | Frye et al. .................... 436/73 |
| 5,618,911 A | 4/1997 | Kimura et al. ............... 528/361 |
| 5,624,875 A | 4/1997 | Nakanishi et al. ............ 501/39 |
| 5,645,632 A | 7/1997 | Pavlin ...................... 106/31.29 |
| 5,667,568 A | 9/1997 | Sacripante et al. ........ 106/20 R |
| 5,804,682 A | 9/1998 | Fischer et al. .............. 528/310 |
| 5,807,968 A | 9/1998 | Heinrich et al. ............ 528/310 |
| 5,852,118 A | 12/1998 | Horrion et al. ............... 525/90 |
| 5,888,597 A | * 3/1999 | Frey .......................... 428/35.5 |
| 5,902,841 A | 5/1999 | Jaeger et al. ................ 523/161 |
| 5,932,630 A | 8/1999 | Kovacs et al. .............. 523/161 |
| 5,936,044 A | * 8/1999 | Melot .......................... 525/432 |

FOREIGN PATENT DOCUMENTS

| | | |
|---|---|---|
| EP | 0 224 389 B1 | 6/1987 |
| EP | 0 373 878 A2 | 6/1988 |
| EP | 0 384 208 B1 | 8/1990 |
| EP | 0 451 954 A2 | 10/1991 |
| EP | 0 470 364 A2 | 2/1992 |
| EP | 0 483 054 A1 | 5/1992 |
| EP | 0 527 613 A2 | 2/1993 |
| EP | 0 566 755 B1 | 6/1996 |
| WO | WO 88/00603 | 1/1988 |
| WO | WO 90/05910 | 5/1990 |
| WO | WO 97/39151 | 10/1997 |

OTHER PUBLICATIONS

"Jeffamine® D–2000 Polyoxypropylenediamine," Huntsman Corporation, Houston, TX, 1994. [Regarding CAS Reg. No. 9046–10–0].
"Jeffamine® D–230 Polyoxypropylenediamine," Huntsman Corporation, Houston, TX, 1997. [Regarding CAS Reg. No. 9046–10–0].
"Jeffamine® D–400 Polyoxypropylenediamine," Huntsman Corporation, Houston, TX, 1998. [Regarding CAS Reg. No. 9046–10–0].
"Jeffamine® EDR–148 Triethyleneglycoldiamine," Huntsman Corporation, Houston, TX, 1994. [Regarding CAS Reg. No. 929–59–9].
"XTJ–502 Poly(Oxyethylene)Diamine," Huntsman Corporation, Houston, TX, 1996. [Regarding CAS Reg. No. 65605–36–9].
Eastman Chemical Company—2000; http://www.eastman.com/Product_Information/ProductHome.asp?Eastman-DotCom=True&Product=167. [Accessed Apr. 16, 2000].

* cited by examiner

*Primary Examiner*—Paul R. Michl
(74) *Attorney, Agent, or Firm*—Seed Intellectual Property Law Group PLLC

(57) ABSTRACT

A block copolymer of the formula hydrocarbon-polyether-polyamide-polyether-hydrocarbon is described. The copolymer may be prepared by reacting together reactants that include dimer acid, diamine, and a polyether having both hydrocarbon termination and termination selected from one of amine, hydroxyl and carboxyl. The copolymer may be combined with a solvent to form a gel, where the gel may be transparent and may be incorporated into household and consumer products including antiperspirants.

33 Claims, No Drawings

HYDROCARBON-TERMINATED POLYETHER-POLYAMIDE BLOCK COPOLYMERS AND USES THEREOF

TECHNICAL FIELD OF THE INVENTION

This invention generally relates to organic resins, more particularly to resins having an internal structure comprised of polyamide and polyether, and terminal structure comprised of hydrocarbon. The invention also relates to the preparation of these resins, and their use as, for example, gelling agents for organic solvents.

BACKGROUND OF THE INVENTION

In many commercially important compositions, the consistency of the product is critical to its commercial success. One example is personal care products, which generally contain one or more active ingredients within a carrier formulation. While the active ingredient(s) determine the ultimate performance properties of the product, the carrier formulation is equally critical to the commercial success of the product in that it largely determines the consistency of the product. The rheology of the carrier (also referred to as the "base") largely determines the flow properties of the product, and the flow properties largely determine the manner in which the consumer will apply or use the product.

For example, aluminum chlorohydrate, aluminum-zirconium tetrachlorohydrate, aluminum-zirconium polychlorohydrate complexed with glycine, and aluminum-zirconium complexed with any of trichlorohydrate, octachlorohydrate, and sesquichlorohydrate are metal salts that are commonly used as active ingredients in deodorant and antiperspirant products. Consumers have shown a preference for applying deodorant from a stick form. Thus, the carrier in a stick-form deodorant must be a relatively hard substance, and waxy fatty alcohol such as stearyl alcohol has often been used as the carrier in these products. As another example, the active ingredient in a lipstick is the colorant. A lipstick should not be as hard as a stick deodorant, but of course must maintain its shape when undisturbed at room temperature. A blend of wax and oil is known to provide a consistency that is well suited as a carrier for a lipstick. As a final example, shampoo desirably has a viscosity greater than water, and when the active ingredient(s) in a shampoo does not have a sufficiently high viscosity, a somewhat viscous carrier material is desirably included in the shampoo formulation.

From the above examples, it is seen that formulators of personal care products depend upon the availability of materials having various rheological properties, in order to formulate a successful personal care product. Materials which have a gel-like character, in that they maintain their shape when undisturbed but flow upon being rubbed, are often desired for personal care products.

Transparent (i.e., clear) carriers are desired by formulators who develop a personal care product wherein colorant is an active ingredient, because a transparent carrier (as opposed to an opaque carrier) will minimally, if at all, interfere with the appearance of the colorant. In recent years, consumers have demonstrated an increasing preference for transparent and colorless personal care products such as deodorants and shampoos. There is thus an increasing demand for transparent materials that can provide the rheological properties needed for various personal care products, and particularly which can impart gel-like character to a formulation.

Polyamide resin prepared from polymerized fatty acid and diamine is reported to function as a gellant in formulations developed for personal care products. For example, U.S. Pat. No. 3,148,125 is directed to a clear lipstick carrier composition formed from polyamide resin compounded with a lower aliphatic alcohol and a so-called "polyamide solvent." Likewise, U.S. Pat. No. 5,500,209 is directed to forming a gel or stick deodorant, where the composition contains polyamide gelling agent and a solvent system including monohydric or polyhydric alcohols. Thus, the prior art recognizes to blend certain polyamides with alcohols, to thereby form a gel.

Polar solvents, e.g., ether- and hydroxyl-containing materials which are liquid at or slightly above room temperature, are desirably included in personal care formulations because they are often benign, allow dilution with at least some water, dissolve a wide range of active and inactive formulation ingredients and are relatively inexpensive. Polar solvents are also available in a wide variety of viscosities and grades. However, these solvents typically do not have the rheological properties that are desired in a carrier, e.g., they do not naturally exhibit gel-like character. Furthermore, gelants for this type of solvent are uncommon and often unavailable.

Accordingly, there is a need in the art for materials that can be combined with solvents, and particularly polar solvents, to afford a transparent material that has gel-like character. The present invention provides this and related advantages as described herein.

SUMMARY OF THE INVENTION

In one aspect, the present invention provides a block copolymer of the formula: hydrocarbon-polyether-polyamide-polyether-hydrocarbon. The present invention also provides compositions that include this block copolymer, where such compositions may also include one or more of a diacid, diamine or hydrocarbon-terminated polyether.

In various aspects: the polyamide block includes blocks of the formula

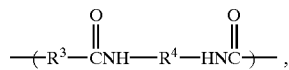

where $R^3$ is a hydrocarbon diradical, preferably dimer acid-derived, e.g., wherein the $R^3$ group includes a diradical that results when two carboxylic acid groups are removed from dimer acid; $R^4$ is selected from a hydrocarbon and a polyether diradical; the polyether block includes blocks of the formula $-(R^2-O)_{}-$, where $R^2$ is a hydrocarbon; $C_{1-22}$ hydrocarbon radicals are located at either end of the copolymer, where the hydrocarbon radical may optionally be selected from alkyl, aralkyl, aryl, and alkaryl radicals.

In other aspects, the copolymer has the formula

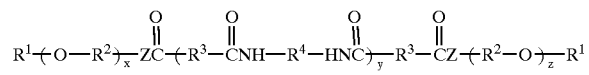

independently at each occurrence, $R^1$ is selected from $C_{1-22}$ hydrocarbon radicals; $R^2$ is selected from $C_{2-6}$ hydrocarbon diradicals; $R^3$ is selected from $C_{2-52}$ hydrocarbon diradicals, where at least 50% of the $R^3$ diradicals have at least 34 carbons; $R^4$ is selected from $C_{2-36}$ hydrocarbon diradicals and $C_4-C_{100}$ polyether diradicals; Z is selected from O and NH; x is an integer from 2 to 100; y is an integer from 1 to 10; Z is NH; $R^2$ is a $C_2$ hydrocarbon diradical; and at least 80% of the $R^3$ diradicals have at least 34 carbon atoms.

In various aspects, the present invention provides a composition that includes a copolymer as described above, that meets one or more of the following criteria: an acid number of less than 25; an amine number of less than 5; a softening point of 50–150° C.; a weight average molecular weight of 2,000 to 20,000; a melting point above 50° C. and a viscosity at 160° C. of less than 5,000 cps.

In another aspect, the present invention provides a process of preparing a block copolymer where the process includes reacting together reactants that include dimer acid, diamine, and a polyether having both hydrocarbon termination and termination selected from one of amine, hydroxyl and carboxyl. The polyether may have the formula $R^1$—(O—$R^2$)$_x$—W where $R^1$ is selected from $C_1$–$C_{22}$ hydrocarbyl, $R^2$ is selected from $C_2$–$C_6$ hydrocarbyl, x is an integer presenting the number of repeating ether units, and W is selected from amine, hydroxyl and carboxyl. The present invention also includes a copolymer and composition prepared by this process.

In another aspect, the present invention provides a gelled composition that includes a hydrocarbon-terminated block copolymer as described above, and a polar organic solvent, the solvent having hydroxyl and/or ether functionality. In a related aspect, the present invention provides a method for preparing a gel, where the method includes combining a hydrocarbon-terminated block copolymer as described above, at elevated temperature with a liquid having hydroxyl and/or ether functionality to provide a mixture, and allowing the mixture to cool to room temperature to form the gel.

In a further aspect, the present invention provides a microemulsion that includes a hydrocarbon-terminated block copolymer as described above, a polar organic solvent, and water.

These and related aspects of the present invention are described more fully herein.

DETAILED DESCRIPTION OF THE INVENTION

In one aspect, the present invention provides a hydrocarbon-terminated block copolymer of the formula (1)

hydrocarbon-polyether-polyamide-polyether-hydrocarbon. (1)

In formula (1), a hydrocarbon group contains only carbon and hydrogen atoms. Suitable hydrocarbon groups are formed from one or more of aliphatic and aromatic moieties. Suitable aliphatic moieties are alkyl, alkylene, alkenyl, alkenylene, alkynyl, alkylnylene, cycloalkyl, cycloalkylene, cycloalkenyl, cycloalkenylene, cycloalkynyl, and cycloalkynylene moieties. Aromatic moieties are also referred to herein as aryl groups. The hydrocarbon group will be referred to herein as $R^1$.

As used herein, alkyl, alkenyl, alkynyl, cycloalkyl, cycloalkenyl, and cycloalkynyl are monovalent radicals, while alkylene, alkenylene, alkynylene, cycloalkylene, cycloalkenylene, and cycloalkynylene are polyvalent radicals. As used herein alkyl, alkylene, cycloalkyl, and cycloalkylene are saturated radicals, while alkenyl, alkenylene, alkynyl, alkylnylene, cycloalkenyl, cycloalkenylene, cycloalkynyl, and cycloalkynylene are unsaturated radicals. The alkyl, alkylene, alkenyl, alkenylene, alkynyl, and alkylnylene moieties may be straight chain or branched. The cycloalkyl, cycloalkenyl, cycloalkynyl, cycloalkylene, cycloalkenylene and cycloalkynylene moieties may be monocyclic or polycyclic, where a polycyclic moiety may be, for example, bicyclic or tricyclic.

Exemplary alkyl moieties are methyl, ethyl, propyl, hexyl, and 2-ethylhexyl. Exemplary alkylene moieties are methylene (—$CH_2$—), methylidene (=$CH_2$), ethylene (—$CH_2CH_2$—). Exemplary cycloalkyl groups are cyclohexyl and norbornyl.

Suitable aromatic moieties are monocyclic or polycyclic. An exemplary monocyclic aryl group is phenyl, while exemplary polycyclic aryl groups are naphthyl and filverenyl. The aromatic moiety may be monovalent, e.g., phenyl, or polyvalent, e.g., phenylene.

The hydrocarbon group may be a combination of aromatic and aliphatic groups. For example, benzyl (phenyl-$CH_2$—, an arylalkylene group), tolyl ($CH_3$-phenylene-, an alkylarylene group), and xylyl (($CH_3$)$_2$phenylene-, a dialkylarylene group). The hydrocarbon group may be a combination of two or more aromatic groups, e.g., biphenyl (phenyl-phenylene-, an arylarylene group).

The $R^1$ group necessarily contains at least one carbon. In one embodiment, the $R^1$ group contains 1–32 carbons. In one embodiment, the $R^1$ alkyl group contains 1–12 carbons. In one embodiment, the $R^1$ group is an alkyl group. In one embodiment, the $R^1$ alkyl group is straight-chained. In one embodiment, the $R^1$ alkyl group is branched.

The block copolymer of formula (1) contains at least two polyether blocks. As its name implies, a polyether block contains a plurality of ether groups, i.e., groups of the formula —C—O—C—. In other words, a polyether block contains the repeating formula —O—$R^2$— where $R^2$ is a hydrocarbon group. In one aspect, $R^2$ is an alkylene group. The alkylene group $R^2$ may be aliphatic (saturated and/or unsaturated) or aromatic, straight chain and/or branched, independently at each occurrence in the polyether block. In one aspect, $R^2$ has 1–6 carbons at each occurrence in the polyether block, while in another aspect $R^2$ has 2–4 carbons at each occurrence. In one aspect, $R^2$ has the formula —$CH_2$—CH($R^{2a}$)— wherein $R^{2a}$ is selected from hydrogen, methyl and ethyl.

In one aspect, the polyether component of the block copolymer has a molecular weight (number or weight average) of less than 10,000. In another aspect, the molecular weight is between 100 and 4,000.

The block copolymer of formula (1) contains a polyamide block. As its name implies, the polyamide block contains a plurality of amide groups, i.e., groups of the formula —NH—C(=O)— and/or —C(=O)—NH—. In the polyamide block, two or more amide groups are separated by hydrocarbon groups, e.g., alkylene groups and/or polyether groups.

In one aspect, the polyamide block contains —C(=O)—$R^3$—C(=O)— moieties wherein $R^3$ is a hydrocarbon group. In one aspect, the polyamide block includes $R^3$ groups having at least 30 carbons. In one aspect, the polyamide block includes $R^3$ groups having 30–42 carbons.

In one aspect, the polyamide block includes $R^3$ groups that are the formed from fatty acid polymerization. Fatty acids derived from vegetable oils, tallow, and tall oil (the latter are known as tall oil fatty acids, or TOFA) are commercially subjected to thermal polymerization, typically in the presence of a clay catalyst, to provide a product known commercially as dimer acid. These fatty acids contain 18 carbons, so that corresponding dimer acid consists mainly of $C_{36}$ dicarboxylic acids. This dimer acid may be denoted by the structure HOOC—$C_{34}$—COOH, where the $C_{34}$ group is an exemplary $R^3$ group of the present invention. $C_{34}$ is a mixture of isomeric structures, as more fully described in detailed descriptions of dimer acid, as found in, for example,

*Naval Stores—Production, Chemistry and Utilization*, D. F. Zinkel and J. Russel (eds.), Pulp. Chem. Assoc. Inc., 1989, Chapter 23.

Suitable polymerized fatty acids are available commercially as, for example, SYLVADYM™ dimer acid and UNIDYME™ dimer acid, both from Arizona Chemical, company of International Paper, (Jacksonville, Fla.), EMPOL™ dimer acid from Henkel Corporation, Emery Oleochemicals Division (Cincinnati, Ohio); and PRIPOL™ dimer acid from Unichema North America (Chicago, Ill.).

Dimer acid, as commercially available, typically contains some by-products of the fatty acid polymerization process. One common byproduct is so-called trimer acid, which results when three fatty acid molecules reaact together to form a $C_{64}$ tricarboxylic acid. It may happen, in the preparation of a block copolymer of the present invention, that two of the carboxylic acid groups of trimer acid will react with, e.g., a diamine, leaving one carboxylic acid group unreacted. When this occurs, the block copolymer will contain a carboxylic acid-substituted $R^3$ group, which is technically not a hydrocarbon. Accordingly, while block copolymers of the present invention contain hydrocarbon groups between two NHC(=O) groups, they may also contain some, typically a minor amount, of carboxylic acid-substituted hydrocarbon groups between two NHC (=O) groups. For convenience, as used herein, $C_{34}$ refers to the incorporation of dimer acid into a polyamide block, where $C_{34}$ includes the reaction product of some trimer acid that may be a by-product in the commercial dimer acid.

In one aspect, the present invention provides block copolymers of formula (1) wherein each of the C(=O) groups is bonded to $C_{34}$, i.e., the block copolymer is formed from dimer acid as the exclusive polyacid reactant. However, in another aspect, the polyamide block includes both $C_{34}$ and "co-diacid"-derived $R^3$ groups. Thus, the polyamide block may be formed by reacting both dimer acid and co-diacid with a diamine.

As used herein, a co-diacid is a compound of formula HOOC—$R^3$—COOH where $R^3$ is not $C_{34}$ as defined above. In one aspect, the polyamide block in copolymers of formula (1) includes $R^3$ groups having 2-32 carbons, which are referred to herein a co-diacid $R^3$ groups. Suitable co-diacid $R^3$ groups include ethylene (from, e.g., succinic acid) and n-butylene (from, e.g., adipic acid).

In one aspect, the $C_{34}R^3$ groups constitute at least 50 mol % of the total of the $R^3$ groups. In other aspects, the $C_{34}R^3$ groups constitute at least 60 mol %, or 70 mol %, or 80 mol %, or 90 mol %, or 95 mol % of the $R^3$ groups. Stated another way, dimer acid contributes at least 50% of the diacid equivalents, or at least 60-%, or 70%, or 80%, or 90%, or 95% of the diacid equivalents in the polyamide block of the copolymer of formula (1).

In one aspect, the polyamide block contains —NH—$R^4$—NH— moieties wherein $R^4$ is a hydrocarbon group. In one aspect, the $R^4$ hydrocarbon groups has 1-20 carbons. In one aspect, the polyamide block includes $R^4$ groups having 1-10 carbons. In one aspect, the $R^4$ group is an alkylene group. In one aspect, $R^4$ is a straight-chained alkylene group. In one aspect, the polyamide block includes $R^4$ groups having 2 carbons, while in another aspect at least 50% of the $R^4$ groups have 2 carbons, while in another aspect all of the $R^4$ groups have 2 carbons.

In one aspect, the polyamide block contains —NH—$R^4$—NH— moieties wherein $R^4$ is a polyether group. As defined above, a polyether block contains a plurality of ether groups, i.e., groups of the formula —C—O—C—. In other words, a polyether block contains the repeating formula —O—$R^2$— where $R^2$ is a hydrocarbon group. In one aspect, $R^2$ is an alkylene group. The alkylene group $R^2$ may be aliphatic (saturated and/or unsaturated) or aromatic, straight chain and/or branched, independently at each occurrence in the polyether block. In one aspect, $R^2$ has 1-6 carbons at each occurrence in the polyether block, while in another aspect $R^2$ has 2-4 carbons at each occurrence. In one aspect, $R^2$ has the formula —$CH_2$—CH($R^{2a}$)— wherein $R^{2a}$ is selected from hydrogen, methyl and ethyl.

In one aspect, the polyether component of the $R^4$ potion of the block copolymer of the present invention has a molecular weight (number or weight average) of less than 10,000. In another aspect, the molecular weight is between 100 and 4,000.

Compounds of the formula $H_2N$—$R^4$—$NH_2$ are commonly known as diamines, and are available from a large number of vendors. Compounds of the formula HOOC—$R^3$—COOH are commonly known as diacids, or dibasic acids, and are likewise available from a large number of vendors. Aldrich (Milwaukee, Wis.; www.sigma-aldrich.com); EM Industries, Inc. (Hawthorne, N.Y.; http://www.emscience.com); Lancaster Synthesis, Inc. (Windham, N.H.; http://www.lancaster.co.uk) are three representative vendors.

In formula (1), the bond '—' between hydrocarbon and polyether represents a C—O bond where the carbon is contributed by the hydrocarbon and the oxygen is contributed by the polyether.

In formula (1), in one aspect, the bond between polyether and polyamide is C—NH—C(=O)—C where C—NH may be seen as being contributed by the polyether and C(=O)—C may be seen as being contributed by the terminal acid group of a polyamide. Block copolymers according to this aspect may be formed by, for example, reacting an amino and hydrocarbon terminated polyether of the formula $R^1$—(O—$R^2$—)$NH_2$ with a carboxylic acid terminated polyamide of the formula HOOC—NH—$R^4$—NH- etc. so as to form $R^1$—(O—$R^2$—)N—C(=O)—$R^4$. Thus, an amide group may be present as the link between polyether and polyamide in formula (1).

In formula (1), in one aspect, the bond between polyether and polyamide is C—C(=O)—NH—C where C—C(=O) may be seen as being contributed by the polyether and NH—C may be seen as being contributed by the terminal amine group of a polyamide. Block copolymers according to this aspect may be formed by, for example, reacting a carboxylic acid and hydrocarbon terminated polyether of the formula $R^1$—(O—$R^2$—)COOH with an amine terminated polyamide of the formula $H_2N$—$R^4$—NH—C(=O)—$R^3$- etc. so as to form $R^1$—(O—$R^2$—)—C(=O)—NH—$R^4$—NH—C(=O)—$R^3$-etc. Thus, once again, an amide group may be present as the link between polyether and polyamide in formula (1).

In formula (1), in one aspect, the bond between polyether and polyamide is C—O—C(=O)—C where C—O may be seen as being contributed by the polyether and C(=O) may be seen as being contributed by the terminal acid group of a polyamide. Block copolymers according to this aspect may be formed by, for example, reacting a hydroxyl and hydrocarbon terminated polyether of the formula $R^1$—(O—$R^2$—) OH with a carboxylic acid terminated polyamide of the formula HOOC—NH—$R^4$—NH-etc. so as to form $R^1$—(O—$R^2$—)O—C(=O)—$R^4$. Thus, an ester group may be present as the link between polyether and polyamide in formula (1).

In one aspect, the present invention provides a composition comprising a hydrocarbon-terminated polyether-polyamide block copolymer of the present invention having an acid number of less than 25, or less than 20, or less than 15, or less than 10. The hydrocarbon-terminated polyether-polyamide block copolymer of formula (1) does not have any free carboxylic acid groups, and accordingly has an acid number of zero. However, when prepared from diacid, diamine and hydrocarbon-terminated polyether according to a process described herein, some of the diacid may not react with the diamine and/or polyether, and according the final product may have some unreacted carboxylic acid that will be responsible for the product having an acid number greater than zero. Preferably, the product has a minor amount of this unreacted diacid, and thus has only a small acid number. Esterification catalysts may be used to encourage all of the diacid to react with hydroxyl groups, so as to minimize the amount of free acid, i.e., to reduce the acid number of the product.

In one aspect, the present invention provides a composition comprising a hydrocarbon-terminated polyether-polyamide block copolymer of the present invention having an amine number of less than 25, or less than 20, or less than 15, or less than 10, or less than 5 or less than 2 or less than 1. The hydrocarbon-terminated polyether-polyamide block copolymer of formula (1) does not have any free amine groups, and accordingly has an amine number of zero. However, when prepared from diacid, diamine and hydrocarbon-terminated polyether according to a process described herein, some of the diamine may not react with the diacid, and according the final product may have some unreacted amine groups that will be responsible for the product having an amine number greater than zero. Preferably, the product has a minor amount of this unreacted diamine, and thus has only a small amine number. Amidification catalysts may be used to encourage all of the diamine to react with carboxyl groups, so as to minimize the amount of free amine, i.e., to reduce the amine number of the product.

In one aspect, the present invention provides hydrocarbon-terminated polyether-polyamide block copolymers, and compositions containing these copolymers, that has a softening point of 50–150° C. (Ring and Ball, or Mettler). In another aspect, the softening point is 75–125° C., while in another aspect the softening point is 75–100° C., while in another aspect the softening point is 80–120° C.

In one aspect, the present invention provides hydrocarbon-terminated polyether-polyamide block copolymers, and compositions containing these copolymers, that has a weight or number average molecular weight of 2,000 to 30,000. The molecular weight is measured by preparing a solution of the copolymer or composition in a suitable solvent, e.g., tetrahydrofuran (THF) and identifying the retention time of the copolymer by gel permeation chromatography, and comparing that retention time to the retention times of solutions of polystyrene having known molecular weight characterizations. In one aspect, the copolymers have a weight or number average molecular weight of greater than 1,000. Among other features, the hydrocarbon termination on the polyether reactant allows for control of the molecular weight of the copolymer. If both ends of the polyether reactant were reactive, e.g., the polyether contained hydroxyl functionality at both ends, then the polyether could not be utilized as a terminator in the preparation of copolymers of the present invention.

In one aspect, the present invention provides hydrocarbon-terminated polyether-polyamide block copolymers, and compositions containing these copolymers, that have a viscosity, as measured on the neat copolymer or composition at 160° C., of less than 5,000 centipoise (cPs, or cps), or less than 4,000 cPs, or less than 3,000 cPs, or less than 2,000 cPs, or less than 1,000 cPs Typically, the copolymer and compositions will have a melt viscosity, as measured on the neat copolymer or composition at 160° C., of more than 50 cPs, typically more than 500 cPs.

Block copolymers of the present invention may be prepared by reacting together compounds of the formulae $R^1$—(O—$R^2$)$_x$—W, HOOC—$R^3$—COOH, and $H_2N$—$R^4$—$NH_2$, where W represents either an amine, hydroxyl or carboxylic acid group. As used herein an amine group (—$NH_2$), a carboxylic acid group (—COOH) and a hydroxyl group (—OH) include reactive equivalents thereof. For instance, HOOC—$R^3$—COOH includes reactive equivalents, such as monoesters and diesters, i.e., compounds wherein a carboxylic acid is in esterified form.

Compounds of the formula $R^1$—(O—$R^2$)$_x$—W wherein W is hydroxyl are also known as ether-terminated polyalkylene glycols. These compounds are generally well known and may be readily prepared by methodology described in the scientific and patent literature. For example, a monohydric initiator, i.e., a compound of the formula $R^1$—OH is reacted with an alkylene oxide (an $R^2$ group that includes an epoxide group), e.g., ethylene oxide, propylene oxide, etc. to provide a compound of the formula $R^1$—(O—$R^2$)$_x$—OH. These compounds are available from, e.g. Aldrich Chemical (Milwaukee, Wis.).

In one aspect, block copolymers are prepared from compounds of formula $R^1$—(O—$R^2$)$_x$—W wherein W is hydroxyl and $R^2$ is ethylene (—$CH_2CH_2$—). Such compounds of formula $R^1$—(O—$R^2$)$_x$—W may be referred to herein as ethoxylates or alcohol ethoxylates. Ethoxylates may be obtained from many commercial sources (e.g., Dow, Midland Mich.) or may be prepared by reacting alcohols of formula $R^1$—OH with ethylene oxide to give the structure (2) below

$$R^1\text{—O—}(CH_2CH_2O)_x\text{—H} \qquad (2)$$

where $R^1$ is a hydrocarbon group as defined previously, and in one aspect is a $C_{6-22}$ alkyl or aralkyl group. Ethoxylates are typically colorless liquids to low melting point pasty solids depending on the chain length (m). Exemplary ethoxylates having various combinations of $R^1$ groups and molecular weight are given in TABLE A (TABLE A—TYPICAL ETHOXYLATES AND THEIR PROPERTIES). In TABLE A, Manuf. is an abbreviation for manufacturer, EO is an abbreviation for ethylene oxide, %EO refers to the weight percent ethylene oxide in the product, EO/OH refers to the molar ratio of ethylene oxide to hydroxyl, HLB refers to the hydrophile lipophile balance, Shell refers to the Shell Chemical division of the Royal Dutch/Shell Group of Companies (www.shell.com) where Shell sells alcohol ethoxylates under the NEODOL™ trademark. Also in TABLE B, Condea refers to CONDEA Vista Company (Houston, Tex.; www.condea.de) which sells a number of alcohol ethoxylates under their brandnames NONFIX™, BIODAC™, LORODAC™, LIALET™, EMULDAC™ and ALFONIC™ where these materials differ by the $R^1$ group, and the number of ethylene oxide groups in the product.

TABLE A

Typical Ethoxylates and Their Properties

| Ethoxylate | Manuf. | $R^1$ | % EO | EO/OH | MW | HLB |
|---|---|---|---|---|---|---|
| NEODOL™ 23-6.5 | Shell | $C_{12-13}$ | 60 | 6.6 | 484 | 12 |
| NEODOL™ 45-13 | Shell | $C_{14-15}$ | 71.8 | 12.9 | 790 | 14.4 |
| NEODOL™ 91-8 | Shell | $C_{9-11}$ | 69.7 | 8.3 | 524 | 13.9 |
| ALFONIC™ 610-3.5 | Condea | $C_{6-10}$ | 50 | 3.1 | 276 | 10 |
| ALFONIC™ 1618-5 | Condea | $C_{16-18}$ | 46 | 5.1 | 469 | 9 |

In another aspect, block copolymers are prepared from compounds of formula $R^1$—(O—$R^2$)$_x$—W wherein W is hydroxyl and $R^2$ is one or both of ethylene (—$CH_2CH_2$—), propylene (—$CH_2$—$CH(CH_3)$—), and n-butylene (—$CH_2CH_2CH_2CH_2$—). Such compounds of formula $R^1$—(O—$R^2$)$_x$—W may be referred to herein as polyalkyl glycols. Polyalkyl glycols may be obtained from many commercial sources (e.g., Dow, Midland Mich.; Union Carbide, Danbury, Conn.; Aldrich, Milwaukee, Wis.) or may be prepared by reacting alcohols of formula $R^1$—OH with ethylene oxide and/or propylene oxide to give the structure (3) below.

$$R^1\text{—}[O(CH_2CH_2O)_x(CH_2CH(CH_3)O)_Y]H \quad (3)$$

As commercially available, $R^1$ is commonly methyl or n-butyl, but $R^1$ can be any hydrocarbon group. Some typical properties of these materials which are available from Union Carbide and Dow are given in TABLE B (TABLE B—TYPICAL GLYCOLS AND THEIR PROPERTIES). These materials are also available as the copolymers of ethylene and propylene glycol. In TABLE B, MPEG stands for methyl ether poly(ethylene glycol) (i.e., the repeating unit is always ethylene so that Y=0) MBPPG stands for monobutyl ether poly(propylene glycol) (i.e., the repeating unit is always propylene so that X=0), and MBPEGCPG stands for monobutyl ether poly(ethylene glycol-co-propylene glycol), 50/50 PPG/PPE (i.e., the repeating unit is selected from ethylene and propylene, so that X and Y are each equal to or greater than 1).

TABLE B

Typical Polyalkyl Glycols and Their Properties

| Glycol | Manuf. | $R^1$ | R' | MW | $T_m$ (° C.) or Visc @ 20° C. (cSt) |
|---|---|---|---|---|---|
| MPEG 350 | DOW | $CH_3$ | H | 350 | −8 |
| MPEG 550 | DOW | $CH_3$ | H | 550 | 20 |
| MPEG 750 | DOW | $CH_3$ | H | 750 | 30 |
| MPEG 2000 | Aldrich | $CH_3$ | H | 2000 | 52 |
| MBPPG 340 | Aldrich | $CH_3(CH_2)_3$ | $CH_3$ | 340 | 20 |
| MBPPG 1000 | Aldrich | $CH_3(CH_2)_3$ | $CH_3$ | 1000 | 140 |
| MBPPG 2500 | Aldrich | $CH_3(CH_2)_3$ | $CH_3$ | 2500 | 1,300 |
| MBPEGCPG 1700 | Aldrich | $CH_3(CH_2)_3$ | H/$CH_3$ | 1700 | 350 |

TABLE B-continued

Typical Polyalkyl Glycols and Their Properties

| Glycol | Manuf. | $R^1$ | R' | MW | $T_m$ (° C.) or Visc @ 20° C. (cSt) |
|---|---|---|---|---|---|
| MBPEGCPG 3900 | Aldrich | $CH_3(CH_2)_3$ | H/$CH_3$ | 3900 | 3,600 |

In another aspect, block copolymers are prepared from hydrocarbon-terminated polyethers of the formula $R^1$—(O—$R^2$)$_x$—W wherein W is carboxylic acid, which are also known as oxa acids. These compounds are generally well known and may be readily prepared by methodology described in the scientific and patent literature. For example, a monohydric initiator, i.e., a compound of the formula $R^1$—OH is reacted with an alkylene oxide (an $R^2$ group that includes an epoxide group), e.g., ethylene oxide, propylene oxide, etc. to provide a compound of the formula $R^1$—(O—$R^2$)$_x$—OH. This ether-terminated polyalkylene glycol is the subjected to oxidation conditions to convert the terminal hydroxyl group to a carboxylic acid group. Oxa acids have the structure (4) below:

$$R^1\text{—}O\text{—}(CH_2CH_2O)_x\text{—}CH_2\text{—}COOH \quad (4).$$

Compounds of formula (4) where m=1 and 2 are available from Hoechst (now Aventis), as experimental products. Some properties of these acids are give in TABLE C (TABLE C—TYPICAL OXA ACIDS AND THEIR PROPERTIES). In TABLE C, AN stands for acid number.

TABLE C

Typical Oxa Acids and Their Properties

| Acid | m | MW | Visc @ 20° C. (mP) | AN (mg KOH/g) |
|---|---|---|---|---|
| 3,6-dioxaheptanoic acid | 1 | 134.1 | 35 | 410 |
| 3,6,9-trioxadecanoic acid | 2 | 178.2 | 73 | 310 |

In another aspect, block copolymers are prepared from compounds of formula $R^1$—(O—$R^2$)$_x$—W wherein W is amine and $R^2$ is one or more of ethylene (—$CH_2CH_2$—), propylene (—$CH_2$—$CH(CH_3)$—), and n-butylene (—$CH_2$—$CH(CH_2CH_2)$—). Such compounds of formula $R^1$—(O—$R^2$)$_x$—W may be referred to herein as polyoxyalkyleneamines. These compounds are generally well known and may be readily prepared by methodology described in the scientific and patent literature. For example, a monohydric initiator, i.e., a compound of the formula $R^1$—OH is reacted with an alkylene oxide (an $R^2$ group that includes an epoxide group), e.g., ethylene oxide, propylene oxide, etc. to provide a compound of the formula $R^1$—(O—$R^2$)$_x$—OH. This ether-terminated polyalkylene glycol is the subjected to reaction conditions to convert the terminal hydroxyl group to a terminal amino group.

Generally, polyoxyalkyleneamines (also known as poly(oxyalkylene) monoamines) have the structure (5) below $$R^1\text{—}OCH_2CH_2O\text{—}(CH_2CHR'O)_x\text{—}CH_2CH(R'')NH_2 \quad (5)$$

where R is preferably an alkyl group; R' is preferably H, $CH_3$, or $C_2H_5$; and R" is preferably H or $CH_3$. Commonly available polyoxyalkyleneamines are typically prepared from ethylene oxide and/or propylene oxide and are available commercially in varying ratios of propylene oxide to ethylene oxide-based residues. Polyoxyalkyleneamines may be obtained from, e.g., BASF, Mt.Olive, N.J. and Huntsman Chemical, Salt Lake City, Utah. Commercially available polyoxyalkyleneamines and selected properties are given in TABLE D (TABLE D—TYPICAL POLYOXYALKYLENEAMINES AND THEIR PROPERTIES). In TABLE D, both the XTJ and JEFFAMINE™ tradenames are used by Huntsman Chemical.

TABLE D

Typical Polyoxyalkyleneamines and Their Properties

| amine | $R^1$ | $R''$ | PO/EO (mole ratio) | MW | $T_m$ (° C.) |
|---|---|---|---|---|---|
| XTJ-505 | $CH_3$ | $CH_3$ | 9/1 | 600 | -40 |
| XTJ-506 | $CH_3$ | $CH_3$ | 3/19 | 1,000 | 29 |
| XTJ-507 | $CH_3$ | $CH_3$ | 39/6 | 2,000 | -36 |
| JEFFAMINE ® M-2070 | $CH_3$ | $CH_3$ | 10/32 | 2,000 | 17 |
| XTJ234 | $CH_3$ | $CH_3$ | 8/49 | 3000 | 36 |
| Diglycol amine | H | H | 0/2 | 105 (m = 0) | |

The diamine may be a polyether diamine, also referred to herein as a PAO (for polyalkyleneoxy) diamine. Polyetherdiamines may be obtained from Huntsman Chemical. A suitable polyether diamine is a poly(propyleneoxy)diamine such as JEFFAMINE® D-400. Another suitable diamine is a poly(ethyleneoxy)-co-propyleneoxy) diamine such as HUNTSMAN XTJ-500. Yet another suitable diamine is JEFFAMINE® EDR-148, which is also known as triethyleneglycoldiamine, having CAS Registry No. 929-59-9 and the chemical structure $H_2N-CH_2CH_2-O-CH_2CH_2-O-CH_2CH_2-NH_2$. In one embodiment, the polyetherdiamine has the structure $NH_2CH(CH_3)CH_2O-(CH_2CHR'O)_x-CH_2CH(CH_3)NH_2$, where R and R' are methyl or H.

Use of a significant level of both polyether diamine and polyether monoamine provides resins having the ability to form clear solutions and/or clear gels in a wide range of polar solvents including propylene glycol, ethanol, polypropylene glycol and polyethylene glycol and their monoalkyl ethers. At high weight percentage use levels of terminator (i.e., hydrocarbon-terminated polyether), the resins are extremely soft. As the total level of polyether in the polyamide block decreases, the resin gains the feel and flexibility of a polyamide prepared from ethylene diamine and dimer acid, thus retaining some softness even at low levels of polyether. Some of these resins may dissolve in ethanol, but most demonstrated good solubility in propanol, however gelling behavior was infrequent. In general, propylene glycol is a preferred solvent to prepare gels from solvent and resins of the invention (i.e., resins prepared from polyether diamine and polyether monoamine). In general, formation of dimer-acid based polyamides, even those including a significant level of both polyether diamine and polyether monoamine among the reactants leads to a resin that it not particularly compatible with glycerol.

When a polyether diamine and polyether monoamine-derived resin is dissolved in a polar solvent, and then this solution is diluted with water, it is typically observed that the solution remains homogeneous, i.e., the resin does not precipitate. Frequently, upon dilution with water, the resin/polar solvent/water mixture takes on a bluish cast, indicating the presence of a microemulsion form.

In preparing the resins of the present invention, it may be noted that the diamine may be a mixture of hydrocarbon diamine and polyether diamine. In addition, it is generally observed that increasing the level of termination, i.e., increasing the relative amount of monoreactive hydrocarbon-terminated polyether, tends to provide a resin with a relatively lower softening point and melt viscosity. The use of hexamethylene diamine (HMDA), in lieu of some or all of ethylene diamine (EDA), tends to lower the softening point of the resin. The inclusion of co-diacid, i.e., diacid other than dimer acid, e.g., sebacic acid, in the reaction mixture tends to raise the softening point of the resulting resin. The polyether monoamine should not contain any hydroxyl groups. The inclusion of hydroxyl groups is detrimental to the gelling ability of the resin made from the monoamine. Accordingly, hydroxyl terminated polyethers are not included within the polyether monoamine reactants of the present invention.

Some of the inventive resins, particularly those prepared from polyether diamines and polyether hydrocarbon-terminated monoamines, have the unusual ability to form microemulsions in mixtures of water and a polar solvent. These blends are clear and homogeneous but have a distinct blue cast and can be either immobile gels or fluid liquids, depending on the concentration of the resin and the polar solvent. They can be diluted with water without formation of a precipitate. Block copolymers of the present invention that form such microemulsions may be particularly useful as corrosion inhibitors in aqueous systems.

As described herein, diamines, dicarboxylic acids, and hydrocarbon-terminated polyethers having a reactive group W selected from hydroxyl, amine and carboxyl are preferred starting materials to form the triblock copolymers of the invention. These starting materials are preferably reacted together with a stoichiometry, and under reaction conditions, such that the acid number of the resulting block copolymer is less than 25, preferably less than 15, and more preferably less than 10, while the amine number is preferably less than 10, more preferably less than 5, and still more preferably less than 1. The softening point of the block copolymer is preferably greater than room temperature, more preferably is about 50° C. to about 150° C., and still more preferably is about 75° C. to about 125° C.

It is important to control the stoichiometry of the reactants in order to prepare a block copolymer according to the invention. The following discussion regarding reactant stoichiometry uses the terms "equivalent(s)" and "equivalent percent", where these terms are intended to have their standard meanings as employed in the art. However, for additional clarity, it is noted that equivalents refer to the number of reactive groups present in a molar quantity of a molecule, such that a mole of a dicarboxylic acid (e.g., sebacic acid) has two equivalents of carboxylic acid, while a mole of monoamine has one equivalent of amine. Furthermore, it is emphasized that in preparing a triblock copolymer of the invention, the diacid has only two reactive groups (both carboxylic acids, although dimer acid may contain a small amount of tricarboxylic acid), the diamine has only two reactive groups (both primary amines) and the hydrocarbon terminated polyether reactant has a single reactive group selected from amine, hydroxyl and carboxyl. Furthermore, these are preferably, although not necessarily, the only reactive materials present in the reaction mixture.

When co-diacid is employed to prepare a block copolymer, the co-diacid preferably contributes no more than about 50% of the equivalents of carboxylic acid present in the reaction mixture. Stated another way, the co-diacid contributes from 0–50 equivalent percent of the acid equivalents in the reaction mixture. Preferably, the co-diacid contributes 0–30 equivalent percent, and more preferably contributes 0–10 equivalent percent of the acid equivalents in the reaction mixture.

The stoichiometry of the reactants will have a significant impact on the composition of the block copolymer. For example, triblock copolymers made with increasing amounts of polyether will tend to have lower (number and weight) average molecular weights. On the other hand, as less polyether is used, the average molecular weight of the molecules that comprise the block copolymer will increase. In general, increasing the average molecular weight of the copolymer will tend to increase the melting point and melt viscosity of the copolymer. When a high melting point copolymer is combined with a solvent to thereby form a gel, the gel will tend to have a firmer consistency than does a gel formed from a copolymer with a low melting point.

In order to prepare a block copolymer of the present invention, the above-described reactants (diacid, diamine and polyether, or reactive equivalents thereof) may be combined in any order. In one embodiment of the invention, the reactants are simply mixed together and heated for a time and at a temperature sufficient to achieve essentially complete reaction, to thereby form the block copolymer. In another embodiment, the diacid and diamine are reacted together, followed by addition of the monoreactive polyether. During formation of the block copolymer, the diacid and diamine compounds will alternate to form what may be termed an alternating copolymer, i.e., the polyamide block of the block copolymer is an alternating copolymer of diacid and diamine. The terms "complete reaction" and "reaction equilibrium" as used herein have essentially the same meaning, which is that further heating of the product does not result in any appreciable change in the acid or amine numbers of the copolymer.

Thus, the block copolymer may be formed in a one-step procedure, wherein all of the diacid (including co-diacid), diamine and polyether are combined and then heated to about 180–250° C. for a few hours, typically 2–8 hours. When lower temperatures are used, a longer reaction time is typically needed to achieve complete reaction. When the reaction temperature is too high, the reactants and/or products may undergo undesirable thermally-induced decomposition. Typically, the reactants must be exposed to a temperature in excess of 100° C. in order to drive off the water formed by the condensation of the reactants. Since one or more of the reactants may be a solid at room temperature, it may be convenient to combine each of the ingredients at a slightly elevated temperature, and then form a homogeneous mixture prior to heating the reaction mixture to a temperature sufficient to cause reaction between the diacid, diamine and polyether. Alternatively, although less preferably, two of the reactants may be combined and reacted together, and then the third reactant is added followed by further heating until the desired product is obtained. Reaction progress may be conveniently monitored by periodically measuring the acid and/or amine number of the product mixture.

As one example, dimer acid may be reacted with diamine so as to form polyamide, and then this intermediate polyamide may be reacted with polyether to form a hydrocarbon terminated polyether-polyamide-polyether block copolymer.

Because the components of the block copolymer are preferably in reaction equilibrium (due to transamidation and/or transesterifiction reactions), the order in which the reactants are combined typically does not impact on the properties of the product copolymer.

Any catalyst that may accelerate amide and/or ester formation between carboxyl, amine and/or hydroxyl groups may be present in the reaction mixture described above. Thus, mineral acid such as phosphoric acid, or tin compounds such as dibutyltin oxide, may be present during the reaction. In addition, it is preferred to remove water from the reaction mixture as it is formed upon amide and, optionally, ester formation. This is preferably accomplished by maintaining a vacuum on the reacting mixture, or by passing a stream of an inert gas (e.g., nitrogen) across the top of the reaction mixture.

The block copolymers of the invention may be used to thicken and/or gel a solvent (where the term "a solvent" includes a mixture of solvents). As used herein, the term solvent includes any substance which is a liquid at a temperature between 10–60° C., and which forms a gel upon being combined with a block copolymer of the present invention. As used herein, the term solvent will be used to encompass oils and other fluids that may be gelled by the block copolymer of the invention, and is not otherwise limited.

The combination of block copolymer and solvent has a gel-like consistency. In general, materials that have a gel-like character will maintain their shape when undisturbed but flow upon being rubbed. Gels prepared with block copolymers of the present invention may be anywhere from soft to hard, where a "hard" gel has a rigid structure and is very resistant to deformation, while a "soft" gel exhibits some, but not too much, resistance to deformation. An illustration of "soft" gel may be seen in the preparation of Jell-O® dessert, which is a well known food product from Kraft Foods Inc. (division of Philip Morris Companies Inc., Northfield, Ill.). When prepared according to the package instructions, Jell-O® dessert is mixed with water to form a relatively soft gel.

The solvent is a liquid at room temperature or slightly above room temperature. A preferred solvent is a polar solvent, where exemplary polar solvents include lower alcohols (e.g., methanol, ethanol, propanol, butanol), glycols, ethers, glycol ethers (i.e., polyalkyleneglycol ethers), and polyols. The polar solvent may be a mixture of solvents. Exemplary polar solvents are described in TABLE E (TABLE E—POLAR SOLVENTS CONTAINING HYDROXYL AND/OR ETHER FUNCTIONALITIES). DOWANOL™ E-200 and E-300 are two exemplary polyethylene glycols from the DOWANOL™ family of glycol ethers from Dow (Midland, Mich.; www.dow.com) while DESMOPHEN™ 550 U and 1600 U are polyether polyols from the DESMOPHEN™ family of products from Bayer Corporation (Pittsburgh, Pa.; www.bayer.com).

TABLE E

| Polar Solvents Containing Hydroxyl and/or Ether Functionalities | | | |
|---|---|---|---|
| Name | CAS | Structure | Functionality |
| Hexylene glycol (a.k.a. 2-methyl-2,4-pentandiol) | 107-41-5 | $CH_3CH(OH)CH_2C(CH_3)_2OH$ | 1 secondary OH 1 tertiary OH |
| Propylene glycol | 57-55-6 | $CH_3CH(OH)CH_2OH$ | 1 primary OH |

TABLE E-continued

Polar Solvents Containing Hydroxyl and/or Ether Functionalities

| Name | CAS | Structure | Functionality |
|---|---|---|---|
| (a.k.a. 1,2-propanediol) | | | 1 secondary OH |
| Ethylene glycol | 107-21-1 | $HOCH_2CH_2OH$ | 2 primary OH |
| Di(propylene glycol) | 25265-71-8 | $HOC_3H_6OC_3H_6OH$ | 2 primary OH's |
| Mixture of 1,2 and 1,3 isomers | | | 2 secondary OH's |
| | | | 1/1 prim/sec OH |
| | | | 1 ether |
| Di(ethylene glycol) ethyl ether | 111-90-0 | $C_2H_5OCH_2CH_2OCH_2CH_2OH$ | 2 ether |
| | | | 1 prim. OH |
| Diethylene glycol dimethyl ether | 111-96-6 | $CH_3OCH_2CH_2OCH_2CH_2OCH_3$ | 3 ether |
| (a.k.a. 2-methoxyethyl ether) | | | |
| DOWANOL ™ E-200 | 25322-68-3 | $H(OCH_2CH_2)_nOH$ | 2 prim. OH |
| Poly(ethylene glycol) MW = 200 | | | ~4 ether |
| DOWANOL ™ E-300 | 25322-68-3 | $H(OCH_2CH_2)_nOH$ | 2 prim. OH |
| Poly(ethylene glycol) MW = 300 | | | ~6 ether |
| DESMOPHEN ™ 1600 U | 25322-69-4 | NOT KNOWN | NOT KNOWN |
| Linear polyether polyol | | | |
| DESMOPHEN ™ 550 U | 25723-16-4 | NOT KNOWN | NOT KNOWN |
| Branched polyether polyol | | | |
| Poly(ethylene glycol) dimethyl ether | 24991-55-7 | $CH_3(OCH_2CH_2)_nOCH_3$ | ~6 ether |
| MW = 250 | | | |

Preferably, the solvent is a polar liquid as described above, and more preferably the solvent is a liquid that contains ether and/or hydroxyl groups. The liquid may contain more than one component, e.g., ether as well as hydroxyl-containing material. In the mixture, the gellant (block copolymer) typically contributes 10–95%, and the solvent typically contributes 5–90%, of the combined weight of the gellant and the solvent. Preferably, the gellant is combined with the solvent such that the weight percent of gellant in the gellant+solvent mixture is about 5–50%, and preferably is about 10–45%. Such gels may be transparent, translucent or opaque, depending on the precise identities of the gellant and solvent, as well as the concentration of gellant in the mixture.

In order to prepare a gel from a solvent and block copolymer, the two components are mixed together and heated until homogeneous. A temperature within the range of about 80–150° C. is typically sufficient to allow the block copolymer to completely dissolve in the solvent. A lower temperature may be used if a solution can be prepared at the lower temperature. Upon cooling, the mixture forms the gelled composition of the invention. Optional components may be added to the molten composition, and are dispersed and/or dissolved to provide a homogeneous composition prior to cooling of the molten composition.

In another embodiment, the block copolymer-containing gels of the present invention may be formulated such that they are transparent. There are various degrees of transparency, ranging from "crystal" clear to hazy, which may be achieved with gels of the invention. In order to provide some measure of the absolute transparency of a gel, the following test has been devised. A white light is shined through a gel sample of a given thickness at room temperature, and the diffuse transmittance and the total transmittance of the light are determined. The percent haze for a sample is determined by the equation: %haze=(diffuse transmittance/total transmittance)×100. Samples are prepared by melting the gel (or product made therefrom) and pouring the melt into 50 mm diameter molds. The samples may be prepared at two thicknesses, e.g., 5.5±0.4 mm and 2.3±0.2 mm.

Clarity measurements are made on a Hunter Lab Ultrascan Sphere Spectrocolorimeter using the following settings: specular included, UV off, large area of view, illuminate D65, and observer 10°. Using this protocol with a 2.3 mm thickness sample, an ATPA gel of the present invention may have a %haze value of less than 75, while paraffin wax has a %haze value of over 90. The %haze value for a gel of the present invention can be increased if desired, by appropriate selection of solvent and gellant. Thus, the present invention provides gels (and articles made therefrom) having a transparency (measured by %haze) of less than 75, preferably less than 50, more preferably less than 25, still more preferably less than 10, and yet still more preferably of 5 or less.

In one embodiment, the gels containing block copolymer of the present invention are also stable, in that they do not display syneresis. As defined in the McGraw-Hill Dictionary of Scientific and Technical Terms ($3^{rd}$ Edition), syneresis is the spontaneous separation of a liquid from a gel or colloidal suspension due to contraction of the gel. Typically, syneresis is observed as the separation of liquid from a gel, and is sometimes referred to as "bleeding", in that wetness is seen along the surfaces of a gel that displays syneresis. From a commercial point of view, syneresis is typically an undesirable property, and the gels of the present invention desirably, and surprisingly do not exhibit syneresis. In one embodiment, the gels of the invention, and articles prepared therefrom, may be stable in the sense that they do not exhibit syneresis. Thus, they do not have an oily feeling when handled.

A gel formed from a block copolymer and the present invention may be used to prepare an antiperspirant or deodorant. The antiperspirant may also contain one or more of aluminum chlorohydrate, aluminum-zirconium tetrachlorohydrate, aluminum-zirconium polychlorohydrate complexed with glycine, and aluminum-zirconium complexed with any of trichlorohydrate, octachlorohydrate, and sesquichlorohydrate. The gels, and the formulated antiperspirant, are preferably transparent.

The block copolymer-containing gels of the invention may be (although need not be) essentially transparent. When transparent, the gels may be combined with colorants (as well as other ingredients) to form lipstick or other cosmetic products, without the gel interfering with or tainting the appearance of the colorant. The gels of the present invention may be combined with aluminum zirconium salts, as well as other ingredients, to form colorless underarm deodorant/antiperspirant, which is currently quite popular. The gels of the invention are also useful in other personal care products, e.g., cosmetics such as eye make-up, lipstick, foundation make-up, costume make-up, as well as baby oil, make-up removers, bath oil, skin moisturizers, sun care products, lip balm, waterless hand cleaner, medicated ointments, ethnic hair care products, perfume, cologne, oral care bases (e.g., for toothpaste) and suppositories.

In addition, the gels of the present invention may be used in household products such as air fresheners, decorative table-top food warmers (i.e., they may be burned slowly to heat, e.g, an overhead chafing dish), automobile wax/polish, candles, furniture polish, metal cleaners/polishes, household cleaners, paint strippers and insecticide carriers.

Formulations to prepare such materials are well known in the art. For example, U.S. Pat. Nos. 3,615,289 and 3,645,705 describe the formulation of candles. U.S. Pat. Nos. 3,148,125 and 5,538,718 describe the formulation of lipstick and other cosmetic sticks. U.S. Pat. Nos. 4,275,054, 4,937,069, 5,069,897, 5,102,656 and 5,500,209 each describe the formulation of deodorant and/or antiperspirant.

The block copolymer of the invention may be incorporated into commercial products such as those listed above, as well as cable filling compounds, urethane/alkyl paint additives, and soaps/surfactants. These products may be prepared by blending the block copolymer with the other components of the product. In these commercial products, the block copolymer will typically be present at a concentration of about 1% to about 50% of the composition, based on the total weight of the composition. It is a routine matter to optimize the amount of block copolymer in a composition, and indeed the amount will vary depending on the actual product and the desired consistency of the product. In general, as more block copolymer is used in a formulation, the product will display a more pronounced gel character, and will form a more rigid, or hard, gel.

The following examples are offered by way of illustration and not by way of limitation.

EXAMPLES

In the following Examples, softening point was measured using a Model FP83HT Dropping Point Cell from Mettler Instruments, Mettler-Toledo International, Inc. (CH-8606 Greifensee, Switzerland; http://www.mt.com), with a heating rate of 1.5° C./min. Techniques to measure acid and amine numbers are well known in the art and need not be described here. See, e.g., ASTM D-465 (1982) from American Society for Testing and Materials (West Conshohocken, Pa.; http://www.astm.org).

EMPOL™ dimer acid is available from Henkel Corporation, Emery Oleochemicals Division (Cincinnati, Ohio; http://www.henkelcorp.com). Ethylene diamine (EDA) is available from Aldrich (Milwaukee, Wis.; www.sigma-aldrich.com). NEODOL™ alcohol ethoxylates are available from Shell Chemical Company (Houston, Tex.; www.shell.com).

Example 1

Hydrocarbyl Ethoxylate-terminated Block Copolymer

A mixture of 67.4 parts EMPOL™ 1008 dimer acid (100 eq. % of acid equivalents), 5.1 parts ethylene diamine (EDA) (72.2 eq. % of amine+hydroxyl equivalents, based on acid equivalents) and 27.4 parts NEODOL™ 23–6.5 alcohol ethoxylate (27.4 eq. % of amine+hydroxyl equivalents, based on acid equivalents) was prepared and heated to about 200–250° C. under a nitrogen atmosphere with simultaneous removal of water. A small amount (ca. 0.1–1.0 parts) hypophosphorous acid was added to minimize coloration of the product. Progress of the reaction was monitored by periodically pulling samples and measuring the acid and/or amine number of the product mixture. A nitrogen sparge was introduced to reduce the amine number to a desired level. The product block copolymer was characterized and found to have an acid number of 18.3 (higher than the theoretical value of 6, indicating incomplete reaction of the alcohol ethoxylate), an amine number of 1.1, a softening point of 90.3° C. and a viscosity at 160° C. of 85 cPs.

Example 2

Hydrocarbyl Ethoxylate-terminated Block Copolymer

The procedure of Example 1 was followed using 57.6 parts EMPOL™ 1008 (100 eq. % acid), 4.4 parts EDA (71.7 eq. % amine+hydroxyl, based on acid equivalents) and 38.0 parts NEODOL™ 45–13 (23.9 eq. % amnine+hydroxyl, based on acid equivalents). The product had an acid number of 16.9 (higher than the theoretical value of 6, indicating incomplete reaction of the alcohol ethoxylate), an amine number of 0.6, a softening point of 92° C. and a viscosity at 160° C. of 94 cPs. The softening point is approximately the same as the block copolymer of Example 1, indicating that ethoxylate molecular weight does not have a large impact on softening point. The gelling behavior of this block copolymer is described in Example 4.

Example 3

Hydricarbyl Ethoxylate-terminated Block Copolymer

The procedure of Example 1 was followed using 47.8 parts EMPOL™ 1008 (100 eq. % acid), 2.8 parts EDA (56.2 eq. % amine+hydroxyl, based on acid equivalents) and 49.4 parts NEODOL™ 45—13 (37.4 eq. % amine+hydroxyl, based on acid equivalents). The product had an acid number of 21.4 (higher than the theoretical value of 6, indicating incomplete reaction of the alcohol ethoxylate), an amine number of 0.4, a softening point of 83.7° C. and a viscosity at 160° C. of 67 cPs. The softening point and melt viscosity are both lower than that of the copolymer of Example 2, indicating that a higher degree of termination reduces the molecular weight of the block copolymer. The gelling behavior of this block copolymer is described in Example 4.

Example 4

Gelling Behavior of Hydrocarbyl Ethoxylate-Terminated Block Copolymer

The copolymers of Examples 2 and 3 were combined with various solvents at a 15 wt % copolymer concentration. The observed gelling properties of the hydrocarbyl-ethoxylate-terminated polyamides are described in TABLE F (TABLE F—GELATION PROPERTIES OF ETHOXYLATE-POLYAMIDES COPOLYMERS AT 15% RESIN). The gelling behavior indicates that the higher level of ethoxylate termination (Example 3) makes the resin more compatible with the polar solvents. This is demonstrated by the fact that the copolymer of Example 2 gels hexylene glycol to form a clear gel, 2-methoxyethyl ether to form an opaque gel, and forms two phases in dipropylene glycol; while the copolymer of Example 3 dissolves in hexylene glycol, forms a clear gel in methoxyethyl ether, and forms an opaque liquid in dipropylene glycol. This indicates that the gelling ability of these resins is a balance between their compatibility (ethoxylate content) and amide content (MW). However, neither of the copolymers of Examples 2 or 3 was capable of gelling propylene glycol, polyethylene glycol, dipropylene glycol. This may be due to the hydrophobic alkyl chain within the ethoxylate molecule. In TABLE F, and elsewhere in the TABLES set forth herein, "ND" indicates not determined.

TABLE F

Gellation Properties of Ethoxylate-Polyamide Copolymers at 15% Resin

| Solvent | Example 2 | Example 3 |
|---|---|---|
| Hexylene glycol | Transl. Gel | Clear liquid |
| Propylene glycol | 2 phases | 2 phases |
| Polyethylene glycol (E-200) | 2 phases | 2 phases |
| Poly(ethylene glycol) dimethyl ether | Opaque gel | Opaque gel |
| Diethylene glycol ethyl ether | Opaque gel | N/D |
| Dipropylene glycol | 2 phases | Opaque liquid |
| 2-Methoxyethyl ether | Opaque gel | Clear gel |

Example 5

Hydrocarbyl Polyalkyl Glycol-terminated Block Copolymer

The procedure of Example 1 was followed using 61.8 parts EMPOL™ 1008 (100 eq. % acid), 4.3 parts EDA (66.5 eq. % amine+hydroxyl, based on acid equivalents) and 33.9 parts MPEG 550 (28.5 eq. % amine+hydroxyl, based on acid equivalents). The product had an acid number of 20.5 (higher than the theoretical value of 6, indicating incomplete reaction of the alcohol ethoxylate), an amine number of 1.0, a softening point of 91° C. and a viscosity at 160° C. of 52 cPs. The gelling behavior of this block copolymer is described in Example 8. At high termination levels (see Examples 6 and 7), the properties of the block copolymer are dominated by the polyalkyl glycol.

Example 6

Hydrocarbyl Polyalkyl Glycol-terminated Block Copolymer

The procedure of Example 1 was followed using 37.3 parts EMPOL™ 1008 (100 eq. % acid), 2.7 parts EDA (68.9 eq. % amine+hydroxyl, based on acid equivalents) and 59.9 parts MPEG 2000 (23.0 eq. % amine+hydroxyl, based on acid equivalents). The product had an acid number of 17.1 (higher than the theoretical value of 6, indicating incomplete reaction of the alcohol ethoxylate), an amine number of 0.4, a softening point of 75.4° C. and a viscosity at 160° C. of 224 cPs. The gelling behavior of this block copolymer is described in Example 8.

Example 7

Hydrocarbyl Polyalkyl Glycol-terminated Block Copolymer

The procedure of Example 1 was followed using 26.1 parts EMPOL™ 1008 (100 eq. % acid), 1.6 parts EDA (56.5 eq. % amine+hydroxyl, based on acid equivalents) and 31.8 parts MBPPG 2500 (31.8 eq. % amine+hydroxyl, based on acid equivalents). The product had an acid number of 17.3 (higher than the theoretical value of 6, indicating incomplete reaction of the alcohol ethoxylate), an amine number of 0.5, a softening point of 41.9° C. and a viscosity at 160° C. of 35 cPs. The gelling behavior of this block copolymer is described in Example 8.

Example 8

Gelling Behavior of Hydrocarbyl Ethoxylate-terminated Block Copolymer

The copolymers of Examples 5, 6 and 7 were combined with various solvents at a 15 wt % copolymer concentration. The observed gelling characteristics of these copolymers is given in TABLE G (TABLE G—GELLATION PROPERTIES OF POLYALKYL GLYCOL-POLYAMIDE COPOLYMERS AT 15% RESIN. The copolymers of Examples 5 and 6 gelled hexylene glycol, but the copolymer of Example 6 gave an opaque gel. The opaque gel is likely caused by the MPEG 2000, which dissolves in hexylene glycol at elevated temperature, but crystallizes out when cooled. This result suggests that the terminal molecule is preferably a liquid that is soluble in the glycol, if a transparent gel is desired. The copolymer of Example 5 gelled the various solvents with combinations of hydroxyl and ether functionality, but was incompatible with polyethylene glycol and propylene glycol. This result suggests that the level of liquid terminator is desirably high in some instances.

However, at >70 wt % of a liquid terminator, the copolymer of Example 7 was a very soft opaque solid that was incompatible with propylene glycol. This behavior may be due to unreacted dimer in the resin that is incompatible with the glycol. Thus, the hydrocarbon-terminated polyalkyl glycol-polyamide block copolymers have excellent gelling properties when a liquid terminator is used and the level of termination is not too great. As with the hydrocarbon-terminated ethoxylate-polyamide copolymers, the gelling characteristics of these resins is a balance between the amide density and polyalkyl glycol content.

TABLE G

Gellation Properties of Polyalkyl Glycol-Polyamide Copolymers at 15% Resin

| Solvent | Example 5 | Example 6 | Example 7 |
|---|---|---|---|
| Hexylene glycol | Clear gel | Opaque gel | ND |
| Propylene glycol | 2 phases | 2 phases | 2 phases |
| Polyethylene glycol (E-200) | 2 phases | 2 phases | ND |
| Diethylene glycol ethyl ether | Transl. gel | ND | ND |
| Poly(ethylene glycol) dimethyl ether | Opaque gel | ND | ND |
| 2-Methoxyethyl ether | Transl. gel | ND | ND |
| Dipropylene glycol | Opaque gel | ND | ND |

Example 9

Hydrocarbyl Oxa Acid-terminated Block Copolymer

The procedure of Example 1 was followed using 74.4 parts EMPOL™ 1008 (75 eq. % acid, based on total acids), 15.7 3,6,9-trioxadecanoic acid (25 eq. % based on total acids) and 9.9 parts EDA (94.7 eq. % amine, based on acid equivalents). The product had an acid number of 11.6, an amine number of 1.1, a softening point of 88.1° C. and a viscosity at 183° C. of 35 cPs. The use of an oxa acid tends to provide a darker colored block copolymer, relative to the use of polyalkyl glycols and alcohol ethoxylates. The gelling behavior of this block copolymer is described in TABLE H below.

TABLE H

Gellation Properties of Oxa Acid-Polyamide Copolymer at 15% Resin

| Solvent | Gel Description |
|---|---|
| 15% in hexylene glycol | Clear gel |
| 15% in Propylene glycol | 2 phases |
| 15% in polyethylene glycol (E-200) | 2 phases |
| 15% in diethylene glycol ethyl ether | Transl. Gel |
| 15% in dipropylene glycol | Opaque gel |
| 15% in poly(ethylene glycol) dimethyl ether | opaque liquid |
| 15% in 2-methoxyethyl ether | Opaque gel |

Examples 10–18

Hydrocarbyl Polyoxyalkyleneamines-Polyamide Block Copolymer

The procedure of Example 1 was followed using EMPOL™ 1008, UNIDYME 18 dimer acid (from Arizona Chemical, Jacksonville, Fla.), EDA, hexamethylene diamine (HMDA, Aldrich), sebacic acid (sebacic, Aldrich), polyoxyalkyleneamine, etc. in the amounts shown in TABLE I. TABLE I also provides the acid number (AN), amine number (AM), softening point in ° C. (s.p. (° C.), molecular weight as determined by gel permeation chromatography using THF as the solvent and reported as both Mn and Mw by reference to polystyrene standards, and viscosity as measured in centipoise at 160° C. (Visc. @ 160° C. (cPs)) for the corresponding product.

Unlike the polyalkyl glycol-polyamide block copolymers, the reactants used to prepare the polyoxyalkyleneamine-polyamide block copolymers react almost completely with the terminator (theoretical acid number=6). Increasing the level of termination (Examples 14 and 13) resulted in a lower softening point and viscosity. The addition of HMDA lowers the softening point (Examples 13 and 17) relative to the use of EDA only, while the addition of sebacic acid as a co-diacid raised the softening point.

The diglycol amine polymer (Example 18) was made by reacting at 180° C. without vacuum in order to only react the amine and not the hydroxyl group. This material was made to determine the effect of free hydroxyl on the gelling characteristics.

The MW of the copolymers as determined by GPC indicates that the copolymers that contain JEFFAMINE™ M-2070 amine have number average MW's ($M_n$) of 4000 to 5000. This result indicates that these resins primarily comprise copolymers having either two or four amide groups, i.e., the resin is primarily a mixture of bis-amide and tetra-amide.

The gelling behavior of this group of block copolymers is described in TABLE J (TABLE J—GELLATION PROPERTIES OF POLYOXYALKYLENEAMINE-POLYAMIDE COPOLYMERS AT 15% RESIN). The copolymers terminated with high levels of >65 wt % M-2070 formed clear or transparent gels in all of the glycols, ethers, and polyols except hexylene glycol, where they dissolved. The addition of sebacic acid raised the softening point of the copolymer, but appeared to make the gels in propylene glycol feel softer. Decreasing the amount of termination (increasing MW) resulted in firmer gels in propylene glycol, but the gels were transparent rather than clear. The use of HMDA versus EDA increased the hardness of the gels in propylene glycol. Thus, the clearest and hardest gels are obtained by using HMDA and the maximum level of termination possible.

Generally, the gel characteristics are related to the level of termination and the density of amide groups. The use of HMDA versus EDA increased the hardness of the gels in propylene glycol. Thus, the clearest and hardest gels are obtained by using HMDA and the maximum level of termination possible. Resins having high levels of M-2070 were slightly soluble in water (at concentrations up to about 3–4%). Thus, these resins are extremely hydrophilic materials and demonstrate some surfactant properties.

TABLE I

Composition and Properties of Polyoxyalkyleneamine-Polyamides

| Example No. | Composition (eq %/wt %) | AN/AM | s.p. (° C.) | MW (GPC) $M_n/M_w$ | Visc. @ 160° C. (cPs) |
|---|---|---|---|---|---|
| 10 | 100/60.0 EMPOL ™, 66.4/4.2 EDA, 28.5/35.8 XTJ 505 | 8.0/0.9 | 93 | | 68.5 |
| 11 | 100/48.4 EMPOL ™, 79.6/4.1 EDA, 14.1/47.6 XTJ 507 | 8.3/0.6 | 103.1 | | 225 |
| 12 | 100/22.5 EMPOL ™ 1008, 44.7/1.1 EDA, 48.5/76.4 JEFFAMINE ™ M-2070 | 7.1/0.5 | 89.2 | | 57.5 |
| 13 | 100/25.7 EMPOL ™, 47.6/1.3 EDA, 40.5/73.0 JEFFAMINE ™ M-2070 | 8.7/0.4 | 89 | 5264/7658 | 59.5 |
| 14 | 100/30.1 EMPOL ™, 57.5/1.8 EDA, 32.3/68.1 M-2070 | 6.2/0.6 | 98.2 | 5078/7804 | 75 |
| 15 | 90/24.6 EMPOL ™, 10/1.0 sebacic, 50.6/1.5 EDA, 38.2/73.0 M-2070 | 8.0/0.3 | 115.5 | 4733/7884 | 63 |
| 16 | 75/21.0 EMPOL ™, 25/2.5 sebacic, 50.8/1.5 EDA, 38.3/75.0 M-2070 | 6.9/0.6 | 140.9 | | 85 |
| 17 | 100/25.5 EMPOL ™, 47.5/2.5 HMDA, 40.5/72.1 M-2070 | 8.7/0.3 | 83 | 4325/7736 | 108 |
| 18 | 100/82.6 UNIDYME ™ 18, 52.9/4.5 EDA, 43.3/12.9 diglycol amine | 9.6/2.5 | 62.9 | 2004/4572 | 171 |

TABLE J

Gellation Properties of Polyoxyalkyleneamine-Polyamides at 15% Resin

| Solvent | Example 10 | Example 11 | Example 13 | Example 14 | Example 15 | Example 17 | Example 18 |
|---|---|---|---|---|---|---|---|
| Hexylene glycol | Clear gel | Transl. gel | Clear liq. | Clear liq. | Clear liq. | Clear liq. | Clear liq. |
| Propylene glycol | 2 phases | 2 phases | Clear gel | Transl. Gel | Clear gel | Clear gel | 2 phases |
| Ethylene glycol | ND | ND | ND | ND | ND | 2 phases | ND |
| Polyethylene glycol (E-200) | 2 phases | 2 phases | Clear gel | Clear gel | Clear gel | Transl. Gel | ND |
| Polyethylene glycol (E-300) | ND | ND | Clear gel | Clear gel | Clear gel | Clear gel | ND |
| Diethylene glycol ethyl ether | Clear gel | ND | ND | ND | ND | ND | ND |
| Dipropylene glycol | Opaque gel | Opaque gel | Clear gel | Transl. Gel | ND | Clear gel | ND |
| Poly(ethylene glycol) dimethyl ether | ND | Transl. Gel | Clear gel | ND | ND | Clear gel | ND |
| 2-methoxyethyl ether | ND | Transl. gel | Clear gel | Transl. gel | ND | Clear gel | Opaque gel |
| DESMOPHEN ™ 1600 U Linear polyether polyol | ND | ND | Clear gel | Transl. Gel | ND | ND | ND |
| DESMOPHEN ™ 550 U Branched polyether polyol | ND | ND | Clear gel | Clear gel | ND | ND | ND |

Examples 19–22

Hydrocarbyl Polyoxyalkyleneamines-Polyamide Block Copolymer

Four resins of the invention were prepared, essentially according to the procedure of Example 1, having the compositions, physical properties and gellation properties as set forth in Table K (Composition and Properties of Poly(oxyalkylene) Monoamine Terminated Polyamides Containing No Co-Diamine).

as the physical properties and gellation properties of the resin, are set forth in TABLE L (Composition and Properties of Poly(oxyalkylene) Monoamine-terminated Polyamides Containing JEFFAMINE® EDR-148).

These resins were prepared by heating about 100 g of the ingredients (total charge) in a 250 mL Erlenmeyer flask in the presence of three drops of 25% aqueous hypophospho-

TABLE K

Composition and Properties of Poly(oxyalkylene) Monoamine Terminated Polyamides Containing No Co-Diamine

| Example No. | Resin Composition EMPOL 1008 - M2070 - EDA (weight %) | AN/ AM | Termination Eq. % on Dimer | Co-Diamine Fraction Total Diamines, Eq. | Propylene Glycol Cut (20 wt %) |
|---|---|---|---|---|---|
| 19 | 22.5 - 76.3 - 1.1 | 2.9/0.6 | 47.8 | 0 | Clear jelly |
| 20 | 25.1 - 73.3 - 1.6 | N.D. | 41.2 | 0 | Clear gel* |
| 21 | 27.1 - 71.1 - 1.8 | N.D. | 37.0 | 0 | Sl. hazy gel* |
| 22 | 24.0 - 74.7 - 1.4 | 1.6/N.D. | 44.0 | 0 | Sl. hazy gel* |

Examples 23–32

Hydrocarbyl Polyoxyalkyleneamines-Polyamide Block Copolymer

A series of resins was prepared having varying amounts of ethylene diamine and polyether diamine (specifically JEFFAMINE® EDR-148). The reactants of these resins, as well rous acid under a gentle nitrogen sweep with stirring. After the mixture reached 220° C., it was held at that temperature for about 3 h. All of these resins were nearly white in color. All of these resins are soft to one degree or another; in general, the the polyalkyleneoxy content, the softer the resin.

TABLE L

Composition and Properties of Poly(oxyalkylene) Monoamine-terminated Polyamides Containing JEFFAMINE ® EDR-148

| Example No. | Resin Composition EMPOL 1008 - M-2070 - EDA - EDR148 (weight %) | Termination Eq. % on Dimer | Co-Diamine Eq. % Total Eq. Diamines | Propylene Glycol Cut (20 wt %) |
|---|---|---|---|---|
| 23 | 26.8 - 70.3 - 0.9 - 2.0 | 37.0 | 46.0 | Clear, weak jelly |
| 24 | 31.1 - 65.2 - 1.4 - 2.2 | 29.6 | 39.4 | Clear jelly |
| 25 | 35.4 - 60.4 - 1.8 - 2.4 | 24.1 | 34.9 | Clear firm gel |
| 26 | 52.4 - 39.3 - 2.4 - 6.0 | 10.6 | 50.0 | Sl. hazy firm gel |
| 27 | 79.6 - 0 - 0 - 20.4 | 0 | 100 | Incompatible |
| 28 | 42.0 - 52.0 - 2.0 - 4.0 | 17.5 | 44.8 | Clear gel |

TABLE L-continued

Composition and Properties of Poly(oxyalkylene) Monoamine-terminated Polyamides
Containing JEFFAMINE ® EDR-148

| Example No. | Resin Composition EMPOL 1008 - M-2070 - EDA - EDR148 (weight %) | Termination Eq. % on Dimer | Co-Diamine Eq. % Total Eq. Diamines | Propylene Glycol Cut (20 wt %) |
|---|---|---|---|---|
| 29 | 82.9 - 0 - 2.7 - 14.4 | 0 | 68.0 | Incompatible |
| 30 | 64.3 - 20.0 - 0 - 15.7 | 4.4 | 100 | Incompatible |
| 31 | 58.5 - 30.0 - 1.6 - 9.9 | 7.2 | 71.3 | Cloudy paste |
| 32 | 45.3 - 46.6 - 1.3 - 6.8 | 14.5 | 53.4 | Clear jelly |

A preferred range of termination, using M-2070, is about 15–18 eq. % with a co-diamine level of about 45–48 eq. % (more than this results in a clear, but mobile "jelly").

Examples 33–38

Hydrocarbyl Polyoxyalkyleneamines-Polyamide Block Copolymer

A series of resins was prepared having varying amounts of ethylene diamine and polyether diamine (specifically JEFFAMINE® D-400). The reactants of these resins, as well as the physical properties and gellation properties of the resin, are set forth in Table M (Composition and Properties of Poly(oxyalkylene) Monoamine-terminated Polyamides Containing JEFFAMINE® D-400.

These resins were prepared by heating about 100 g of the ingredients (total charge) in a 250 mL Erlenmeyer flask in the presence of three drops of 25% aqueous phosphorous acid under a gentle nitrogen sweep with stirring. After the mixture reached 220° C., it was held at that temperature for about 3 h. All of these resins were nearly water white in color. All of these resins are soft to one degree or another; in general, the higher the polyalkyleneoxy content, the softer the resin.

Examples 39–45

Hydrocarbyl Polyoxyalkyleneamines-Polyamide Block Copolymer

A series of resins was prepared having varying amounts of ethylene diamine and polyether diamine (specifically HUNTSMAN XTJ-500 and/or HUNTSMAN XTJ-506). The reactants of these resins, as well as the physical properties and gellation properties of the resin, are set forth in Table N (Composition and Properties of Poly(oxyalkylene) Monoamine-terminated Polyamides Containing HUNTSMAN XTJ-500 and/or HUNTSMAN XTJ-506.)

These resins were prepared by heating about 100 g of the ingredients (total charge) in a 250 mL Erlenmeyer flask in the presence of three drops of 25% aqueous hyposphorous acid under a gentle nitrogen sweep with stirring. After the mixture reached 220° C., it was held at that temperature for about 3 h. All of these resins were nearly white in color. All of these resins are soft to one degree or another; in general, the the polyalkyleneoxy content, the softer the resin.

TABLE M

Composition and Properties of Poly(oxyalkylene) Monoamine-terminated Polyamides
Containing JEFFAMINE ® D-400

| Ex. No. | Resin Composition EMPOL 1008 - M2070 - EDA - Jeff.D400 (weight %) | AN/ AM | Termination Eq. % on Dimer | Co-Diamine Fraction Total Diamines, Eq. | Propylene Glycol Cut (20 wt %) |
|---|---|---|---|---|---|
| 33 | 45.3 - 46.6 - 1.3 - 6.8 | —/— | 16.9 | 36.7 | Clear weak gel |
| 34 | 35.6 - 55.9 - 2.0 - 6.4 | 2.8/0.6 | 22.2 | 30.3 | Clear firm gel |
| 35 | 35.9 - 55.6 - 2.0 - 6.4 | 3.2/1.3 | 21.9 | 30.2 | Clear firm gel |
| 36 | 59.3 - 24.7 - 4.2 - 11.9 | 4.5/0.8 | 5.9 | 28.1 | Cloudy firm gel |
| 37 | 69.8 - 13.8 - 5.6 - 10.8 | —/— | 2.8 | 20.9 | Incompatible |
| 38 | 59.4 - 24.6 - 4.2 - 11.8 | 4.4/0.6 | 5.9 | 28.0 | nd |

Formulations of dimer acid, EDA, M-2070, and D-400 gel propylene glycol over a wide range of compositional space, from about 45–60 wt % dimer, 47–25% monoamine, and 6–12% D-400, adjusted to have a termination level of 6–22 eq. % with about 30–35% eq. replacement of EDA with D-400. Such resins, and formulations to prepare such resins, are a preferred embodiment of the present invention.

The resin of Example 45 represents a block copolymer of the present invention with a high molecular weight and viscosity which still exhibits useful gelation properties, although it is incompatible with propylene glycol. It had a softening point of 96.8° C., MWw of 18,240 daltons and a viscosity at 160° C. of 2,940 cPs. It dissolves in and forms a clear, firm gel with the polar solvent ethyl lactate.

TABLE N

Composition and Properties of Poly(oxyalkylene) Monoamine-terminated Polyamides Containing Huntsman XTJ-500 and/or XTJ-506

| Ex. No. | Resin Components & Composition | Termination Eq. % on Dimer | Co-Diamine Fraction Total Diamines, Eq. | Propylene Glycol Cut (20 wt %) |
|---|---|---|---|---|
| | Empol 1008 - M2070 - EDA - XTJ500 (wt %) | | | |
| 39 | 56.0 - 23.0 - 3.8 - 17.2 | 5.8 | 30.0 | Cloudy firm gel |
| | Empol 1008 - XTJ506 - EDA - Jeff.D400 (wt %) | | | |
| 40 | 59.8 - 25.2 - 3.9 - 11.1 | 12.0 | 28.0 | nd |
| 41 | 42.0 - 49.3 - 2.1 - 6.6 | 33.5 | 29.6 | Clear firm gel |
| 42 | 69.9 - 12.6 - 5.1 - 25.0 | 5.1 | 25.1 | Incompatible |
| | Empol 1008 - XTJ506 - EDA - XTJ500 (wt %) | | | |
| 43 | 63.3 - 15.6 - 4.5 - 16.6 | 7.0 | 25.9 | Incompatible |
| 44 | 73.9 - 4.2 - 6.0 - 16.0 | 1.6 | 20.3 | Incompatible |
| 45 | 70.0 - 6.5 - 5.2 - 18.2 | 2.7 | 20.3 | Incompatible |

All publications and patent applications mentioned in this specification are herein incorporated by reference to the same extent as if each individual publication or patent application was specifically and individually incorporated by reference.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A block copolymer of the formula hydrocarbon-polyether-polyamide-polyether-hydrocarbon.

2. The copolymer of claim 1 wherein the polyamide block comprises the formula

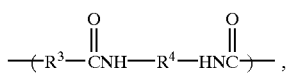

where $R^3$ is a hydrocarbon and $R^4$ is selected from hydrocarbons and polyethers.

3. The copolymer of claim 2 wherein the $R^3$ groups comprise a diradical that results when two carboxylic acid groups are removed from dimer acid.

4. The copolymer of claim 2 wherein the $R^4$ group is a hydrocarbon.

5. The copolymer of claim 2 wherein the $R^4$ group is a polyether.

6. The copolymer of claim I wherein the polyether block comprises the formula

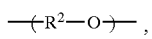

where $R^2$ is a hydrocarbon.

7. The copolymer of claim 1 having $C_{1-22}$ hydrocarbon radicals independently selected at either end of the copolymer.

8. The copolymer of claim 7 wherein the hydrocarbon radical is selected from alkyl, aralkyl, aryl, and alkaryl radicals.

9. The copolymer of claim 1 having the formula

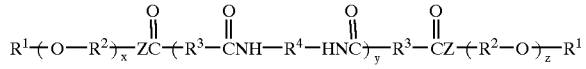

wherein, independently at each occurrence, $R^1$ is a $C_{1-22}$ hydrocarbon radical; $R^2$ is a $C_{2-6}$ hydrocarbon diradicals; $R^3$ is a $C_{2-52}$ hydrocarbon diradical, where at least 50% of the $R^3$ diradicals have at least 34 carbons; $R^4$ is selected from $C_{2-36}$ hydrocarbon diradicals and $C_4$–$C_{100}$ polyether diradicals; Z is selected from O and NH; x is an integer from 2 to 100; and y is an integer from 1 to 10.

10. The copolymer of claim 8 wherein Z is NH.

11. The copolymer of claim 8 wherein $R^2$ is a $C_2$ hydrocarbon diradical.

12. The copolymer of claim 8 where at least 80% of the $R^3$ diradicals have at least 34 carbon atoms.

13. A composition comprising a block copolymer according to claim 1, the composition having an acid number of less than 25.

14. A composition comprising a block copolymer according to claim 1, the composition having an amine number of less than 5.

15. A composition comprising a block copolymer according to claim 1, the composition having a softening point of 50–150° C.

16. A composition comprising a block copolymer according to claim 1, the composition having a weight average molecular weight of 2,000 to 30,000.

17. A composition comprising a block copolymer according to claim 1, the composition having a melting point above 50° C. and a viscosity at 160° C. of less than 5,000 cps.

18. A composition of claim 17 having a viscosity of less than 100 cps.

19. A process of preparing a block copolymer comprising reacting together reactants comprising dimer acid, diamine, and a polyether having both hydrocarbon termination and termination selected from amine, hydroxyl and carboxyl.

20. The process of claim 19 wherein the polyether has the formula $R^1$—(O—$R^2$—)$_x$—W where $R^1$ is selected from $C_1$–$C_{22}$ hydrocarbyl, $R^2$ is selected from $C_2$–$C_6$ hydrocarbyl, and W is selected from amine, hydroxyl and carboxyl, and x is an integer from 2 to about 100.

21. The process of claim 19 wherein the polyether has a number or weight average molecular weight between 100 and 4000.

22. The process of claim 19 wherein the diamine has the formula $H_2N-R^4-NH_2$ and $R^4$ is a $C_{2-36}$ hydrocarbon diradical.

23. The process of claim 22 wherein the diamine is ethylene diamine.

24. The process of claim 19 wherein the diamine has the formula $H_2N-R^4-NH_2$ and $R^4$ has the formula $-R^5-O-R^5-$ wherein $R^5$ is a $C_1-C_6$ hydrocarbon diradical.

25. The process of claim 19 wherein the reactants are exposed to a reaction temperature in excess of 100° C.

26. The process of claim 19 wherein hypophosphorous acid is added to one or more of the reactants.

27. The process of claim 19 wherein the reactants are reacted together until at least one of the following criteria is met: the product has an acid number of less than 25; the product has an amine number of less than 5; the product has a softening point of 50–150° C.; the product has a weight average molecular weight of 2,000 to 30,000; the product has a viscosity at 160° C. of less than 5,000 cps.

28. A composition prepared by the process of claim 19.

29. A gelled composition comprising a hydrocarbon-terminated block copolymer according to claim 1, and a solvent, the solvent having hydroxyl and/or ether functionality.

30. A gelled composition comprising a hydrocarbon-terminated block copolymer resulting from the process of claim 19, and a solvent, the solvent having hydroxyl and/or ether functionality.

31. A method for preparing a gel, comprising combining a hydrocarbon-terminated block copolymer according to claim 1 at elevated temperature with a liquid having hydroxyl and/or ether functionality to provide a mixture, and allowing the mixture to cool to room temperature to form the gel.

32. A composition comprising water, polar organic solvent, and copolymer of claim 1.

33. The composition of claim 32 in the form of a microemulsion.

* * * * *

UNITED STATES PATENT AND TRADEMARK OFFICE
CERTIFICATE OF CORRECTION

PATENT NO.     : 6,399,713 B1
DATED          : June 4, 2002
INVENTOR(S)    : Richard C. MacQueen et al.

It is certified that error appears in the above-identified patent and that said Letters Patent is hereby corrected as shown below:

Column 28,
Line 34, "and y is an integer from 1 to 10." should read -- y is an integer from 1 to 10; and z is an integer from 2-100. --.

Signed and Sealed this

Twenty-first Day of January, 2003

JAMES E. ROGAN
*Director of the United States Patent and Trademark Office*